United States Patent [19]
Alessi et al.

[11] Patent Number: 4,895,862
[45] Date of Patent: Jan. 23, 1990

[54] NOVEL BENZYL-3H-1,2,3,5-OXATHIADIAZOLE 2-OXIDES USEFUL AS ANTIHYPERGLYCEMIC AGENTS

[75] Inventors: Thomas R. Alessi, Monmouth Junction, N.J.; Terence M. Dolak, Canadaigua, N.Y.

[73] Assignee: American Home Products Corp., New York, N.Y.

[21] Appl. No.: 341,407

[22] Filed: Apr. 21, 1989

[51] Int. Cl.[4] .................... C07D 291/04; A01K 31/41
[52] U.S. Cl. ..................................... 514/360; 548/122
[58] Field of Search ......................... 548/122; 514/360

[56] References Cited

U.S. PATENT DOCUMENTS 3,118,903 1/1964 Schmitt ............................... 548/122
4,148,801 4/1979 Santilli ................................. 564/224

OTHER PUBLICATIONS

Eloy, Bull. Soc. Chim., Belger 74 129(1965) Abstract.
A. Dondoni et al, J. Org. Chem., 42 (21), 3372–3377 (1977).
A. Y. Chang et al, Diabetes, 32, 830–838 (1983).

*Primary Examiner*—Robert Gerstl
*Attorney, Agent, or Firm*—Walter Patton

[57] ABSTRACT

This invention relates to novel benzyl-3H-1,2,3,5-oxathiadiazole 2-oxides, to the processes for their preparation, to methods for using the compounds, and to pharmaceutical preparations thereof. The compounds have pharmaceutical properties which render them beneficial for the treatment of diabetes mellitus and associated conditions.

17 Claims, No Drawings

NOVEL BENZYL-3H-1,2,3,5-OXATHIADIAZOLE 2-OXIDES USEFUL AS ANTIHYPERGLYCEMIC AGENTS

BACKGROUND OF THE INVENTION

This invention relates to novel (substituted benzyl)-3H-1,2,3,5-oxathiadiazole 2-oxides, to the processes for their preparation, to methods for using the compounds, and to pharmaceutical compositions thereof. The compounds have pharmaceutical properties which render them beneficial for the treatment of diabetes mellitus and associated conditions.

The serious complications of diabetes mellitus such as nephropathy, retinopathy, neuropathy and cataract are all associated with an excessive amount of blood glucose. The major therapeutic objective is therefore the normalization of blood glucose, both in the fasting and postprandial situations.

The therapeutic approaches to the treatment of Non-Insulin Dependent Diabetes Mellitus (NIDDM, Type II) involve the use of diet, insulin or orally active hypoglycemic agents. Presently, such orally active hypoglycemic agents are chosen (a) from sulfonylureas such as chloropropamide, glyburide and others or (b) biguanides such as metformin and related products. Both these groups of agents have serious disadvantages. Sulfonylureas, upon chronic use, lose their effectiveness. In contrast, biguanides suffer from a serious side effect, lactic-acidosis.

More recently, oxazolidinedione (U.S. Pat. No. 4,342,771) and thiazolidinedione (European Patent Application No. 117,035) derivatives have been described as useful hypoglycemic agents. U.S. Pat. No. 4,461,902 discloses substituted 5-[(4-cyclohexyl-methoxyphenyl)-methyl]thiazolidine-2,4-diones of formula

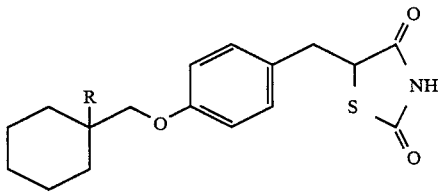

wherein R is methyl (ciglitazone) and related analogues as hypoglycemic agents.

The present invention relates to (substituted benzyl)-3H-1,2,3,5-oxathiadiazole 2-oxides of the structural formula (I)

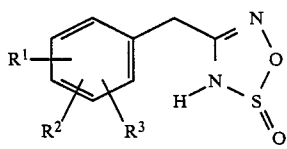

wherein $R^1$, $R^2$ and $R^3$ are independently selected from the group consisting of hydrogen, lower alkyl or alkoxy containing 1 to 6 carbon atoms, halogen, trifluoromethyl, nitro, vinyl, ethynyl, alkylthio, nitrile, phenyl, phenyl- or halogen substituted phenylalkoxy, wherein alkyl contains 1 to 4 carbon atoms and the pharmaceutically acceptable salts thereof.

The preferred compounds of the present invention are those of structural formula (II)

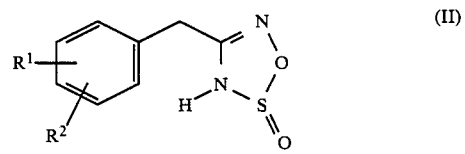

wherein $R^1$ is hydrogen, lower alkyl or alkoxy containing 1 to 2 carbon atoms, halogen or trifluoromethyl; $R^2$ is hydrogen, lower alkyl or alkoxy containing 1 to 6 carbon atoms, halogen, nitro, phenyl, phenyl- or halogen substituted phenyl-alkoxy, wherein alkyl contains 1 to 2 carbon atoms and the pharmaceutically acceptable salts thereof.

The oxathiadiazole 2-oxide portion of the compounds of the present invention can exist in more than one tautomeric form. For clarity, only one of the tautomers is represented in the generic formulas (I) and (II) above. The possible tautomeric forms are listed below:

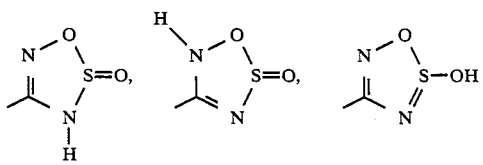

All of said tautomers are included in the present invention. The actual tautomeric form which the compounds of the present invention assume is not known.

This invention also includes mixtures of optically active isomers or partially or completely resolved isomers of the compounds disclosed.

The compounds of this invention are useful as antidiabetic agents for the reduction of blood/plasma sugar levels and for the treatment and/or prevention of diabetic complications and as antihyperlipidemic and antihyperinsulinemic agents.

The most preferred compounds of the present invention are:

4-[(3,4-dimethylphenyl)methyl]-3H-1,2,3,5-oxathiadiazole 2-oxide;

4-[[4-(trifluoromethyl)phenyl]methyl]-3H-1,2,3,5-oxathiadiazole 2-oxide;

4-[[4-(1,1-dimethylethyl)phenyl]methyl]-3H-1,2,3,5-oxathiadiazole 2-oxide;

4-[(1,1'-biphenyl)-4-ylmethyl]-3H-1,2,3,5-oxathiadiazole 2-oxide;

4-[[4-(2-phenylethoxy)phenyl]methyl]-3H-1,2,3,5-oxathiadiazole 2-oxide;

4-[(3-chlorophenyl)methyl]-3H-1,2,3,5-oxathiadiazole 2-oxide;

4-[[(3-trifluoromethyl)phenyl]methyl]-3H-1,2,3,5-oxathiadiazole 2-oxide;

4-[(4-chlorophenyl)methyl]-3H-1,2,3,5-oxathiadiazole 2-oxide;

4-[(4-nitrophenyl)methyl]-3H-1,2,3,5-oxathiadiazole 2-oxide;

4-[(3,4-dimethoxyphenyl)methyl]-3H-1,2,3,5-oxathiadiazole 2-oxide;

4-[[4-(phenylmethoxy)phenyl]methyl]-3H-1,2,3,5-oxathiadiazole 2-oxide;

4-[(4-bromo-2-fluorophenyl)methyl]-3H-1,2,3,5-oxathiadiazole 2-oxide;

4-[[4-[(2-fluorophenyl)methoxy]phenyl]methyl]-3H-1,2,3,5-oxathiadiazole 2-oxide;
and the pharmaceutically acceptable salts thereof.

DETAILED DESCRIPTION OF THE INVENTION

The benzyl-3H-1,2,3,5-oxathiadiazole 2-oxides of this invention may be administered to mammals, for example, man, cattle or rabbits, either alone or in dosage forms, i.e., capsules or tablets, combined with pharmacologically acceptable excipients.

The compounds of this invention may be given orally. However, the method of administering the present active ingredients of this invention is not to be construed as limited to a particular mode of administration. For example, the compounds may be administered orally in solid form containing such excipients as starch, milk, sugar, certain types of clay and so forth. They may also be administered orally in the form of solutions or they may be injected parenterally. For parenteral administration, they may be used in the form of a sterile solution, preferably of pH 7.2–7.6, containing a pharmaceutically acceptable buffer.

The dosage of the benzyl-3H-1,2,3,5-oxathiadiazole 2-oxides will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects.

For oral administration (or as a suppository) to an adult patient, a preferred level of dosage ranges from about 0.01 to 50 mg/kg body weight/day. For parenteral administration to an adult patient, a preferred level of dosage ranges from about 0.005 to 50 mg/kg body weight/day, once daily or divided into 2 to 4 times a week.

Unit dosage forms such as capsules, tablets, pills and the like may contain from about 5.0 mg to about 250 mg of the active ingredients of this invention with a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents, for example, magnesium stearate.

The benzyl-3H-1,2,3,5-oxathiadiazole 2-oxides can also be used in combination with dietary restriction, insulin, sulfonylureas, such as chloropropamide and glyburide, biguanides, such as metformin, aldose reductase inhibitors or hypolipidemic agents to produce a beneficial effect in the treatment of diabetes mellitus. In this instance, commercially available insulin preparations or agents exemplified above are suitable. The compounds hereof can be administered sequentially or simultaneously with insulin or the above exemplified agents. Suitable methods of administration, compositions and doses of the insulin preparations or the above exemplified agents are described in medical textbooks; for instance, "Physicians' Desk Reference", 36 ed., Medical Economics Co., Oradell, N.J., U.S.A., 1982.

The compounds of the present invention are prepared according to the general sequence outlined in Scheme I below:

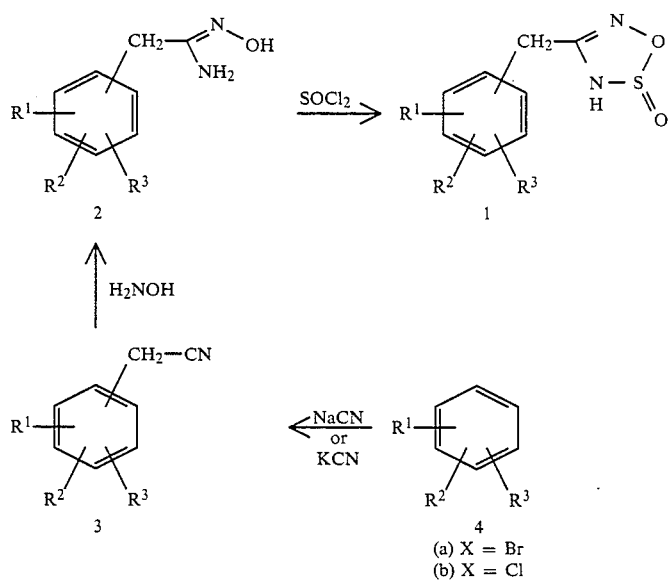

Scheme I

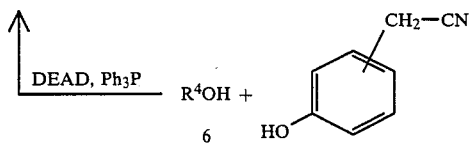

wherein $R^1$, $R^2$ and $R^3$ are as defined above, and $R^4$ is phenyl- or halogen substituted phenylalkyl, wherein alkyl contains 1 to 4 carbon atoms.

All of the oxathiadiazoles 1, are prepared from the corresponding amidoximes 2, by treatment with thionyl chloride by one of two possible methods, either in the presence of an amine base, such as pyridine or triethylamine, at low temperatures ($-23°$ to $5°$ C.), or in the absence of base at temperatures from ambient to $110°$ C. When an amine base is used, the reaction is generally performed in inert organic solvents such as methylene chloride, acetonitrile, or tetrahydrofuran. In the absence of base, higher boiling organic solvents such as benzene or toluene are used. Reaction time ranges from a few minutes to several hours. The oxathiadiazoles are isolated either by concentration of the reaction mixture or by first washing the reaction mixture with water, separating the organic layer and drying before concentrating. Purification is effected either by chromatography on silica gel or recrystallization.

The intermediate amidoximes 2, also have activity as antidiabetic agents. They can exist as either the E or Z isomer, although the Z isomer usually predominates and is more stable. In general, the amidoximes are used without attempting to separate the isomers. The amidoximes are prepared by treatment of the corresponding nitriles 3, with hydroxylamine, the free base of which is liberated from the hydrochloride salt with either sodium methoxide, sodium ethoxide or sodium hydroxide. The reaction is performed in methanol, ethanol or aqueous DMSO at temperatures ranging from ambient to reflux. The amidoximes can be isolated from the reaction mixture either by precipitation via addition of water and subsequent filtration, or by extraction into an organic solvent following removal in vacuo of the reaction solvent. Purification is effected by chromatography on silica gel or recrystallization.

The nitriles 3, required for conversion to the amidoximes, are prepared from the corresponding bromides 4a, or chlorides 4b, by addition of either sodium or potassium cyanide. The addition of cyanide is performed in either ethanol, aqueous acetonitrile or aqueous DMSO from ambient temperature to reflux. The nitriles are isolated by removal of the reaction solvent, followed by partitioning between water and a low boiling organic solvent such as methylene chloride. When DMSO is utilized for the reaction, excess water is added to precipitate the desired product which is collected by filtration. Purification can be effected by chromatography or recrystallization.

Alternatively, the nitriles 3, are prepared from the corresponding hydroxybenzyl cyanide 5, via coupling with an alcohol 6, in the presence of triphenylphosphine and diethylazodicarboxylate (DEAD). These reactions are performed at ambient temperature in an inert organic solvent such as THF. The nitriles 3, are isolated by partitioning between ether and water, separation and drying of the ethereal layer, followed by concentration in vacuo. Purification is effected by chromatography on silica gel.

The chemical bases which are used as reagents in this invention to prepare the aforementioned pharmaceutically acceptable salts are those which form non-toxic salts with the various herein described (substituted benzyl)-3H-1,2,3,5-oxathiadiazole 2-oxides. These particular non-toxic base salts are of such a nature that their cations are said to be essentially non-toxic in character over the wide range of dosage administered. Examples of such cations include those of sodium, potassium, calcium and magnesium. These salts may be prepared by mixing organic solutions of the (substituted benzyl)-3H-1,2,3,5-oxathiadiazole 2-oxides in alcohol and the desired alkali metal alkoxide together and then isolating the resulting salts by removal of the solvent and filtration with a nonpolar solvent. Stoichiometric quantities of reagents must be employed in order to ensure completeness of reaction and maximum production yields with respect to the desired final product.

The following examples further illustrate the present invention.

EXAMPLE 1

4-[(3,4-Dimethylphenyl)methyl]-3H-1,2,3,5-oxathiadiazole 2-Oxide

Step (1) Preparation of N'-Hydroxy-2-(3,4-dimethylphenyl)ethanimidamide 3,4-Dimethylphenylacetonitrile (10 g, 0.069 mol) was added to a mixture of hydroxylamine hydrochloride (9.57 g, 0.14 mol), methanol (100 mL) and 25% sodium methoxide/methanol (31.5 mL, 0.14 mol) at room temperature. After stirring for 16 hours at room temperature, the reaction mixture was concentrated in vacuo. The resultant oil was partitioned between methylene chloride and water. The organic phase was separated, washed with water, dried over magnesium sulfate and concentrated in vacuo to yield the desired product (11.4 g, 93%) as a white solid. Recrystallization from toluene afforded an analytical sample m.p. $59°-60°$ C.

NMR (CDCl$_3$, 200 MHz): δ 1.5 (bs, 2H), 2.2 (s, 6H), 3.5 (s, 2H), 5.4 (bs, 1H), 7.0 (m, 3H).

MS (EI): m/e 178.

Anal. Calcd. for $C_{10}H_{14}N_2O$: C, 67.39; H, 7.92; N, 15.72%. Found: C, 67.39; H, 8.06; N, 15.54%.

Step (2) Preparation of 4-[(3,4-Dimethylphenyl)methyl]-3H-1,2,3,5-oxathiadiazole 2-Oxide Thionyl chloride (17.7 mL, 0.24 mol) in methylene chloride (40 mL) was added dropwise to a solution of N'-hydroxy-2-(3,4-dimethylphenyl)ethanimidamide (10.8 g, 0.06 mol), methylene chloride (130 mL) and pyridine (9.8 mL, 0.12 mol) at $5°$ C. After 3 hours, the mixture was poured into water and the organic layer separated. The organic layer was washed with saturated aqueous sodium chloride, dried over magnesium sulfate and concentrated in vacuo. Recrystallization from ethyl ether afforded the desired product (4.3 g, 32%) as an off-white solid, m.p. 127°–130° C.

NMR (acetone-d$_6$, 400 MHz): δ 2.2 (s, 6H), 2.84 (s, 1H), 3.9 (q, 2H), 7.1 (m, 3H).

MS (EI): m/e 224.

Anal. Calcd. for $C_{10}H_{12}N_2O_2S$: C, 53.55; H, 5.39; N, 12.49%. Found: C, 53.61; H, 5.35; N, 12.42%.

EXAMPLE 2

4-[[4-(2-Phenylethoxy)phenyl]methyl]-3H-1,2,3,5-oxathiadiazole 2-Oxide

Step (1) Preparation of 4-(2-Phenylethoxy)phenylacetonitrile

Diethylazodicarboxylate (DEAD, 7.85 g, 45.1 mmol), was added to a solution of 4-hydroxybenzyl cyanide (5.0 g, 37.6 mmol), phenethylalcohol (5.04 g, 41.3 mmol), and triphenylphosphine (11.82 g, 45.1 mmol) in anhydrous THF (100 mL) at room temperature. A water bath was used to maintain the temperature of the exothermic reaction near ambient. The water bath was removed after 40 minutes and the yellow solution stirred 24 hours. Water was added and the mixture extracted with ether (3×100 mL). The combined organic layers were washed with water (2×75 mL), brine, dried over anhydrous magnesium sulfate and concentrated in vacuo to give an oily yellow solid. The residue was washed with ether, and the resulting white solid removed by filtration. The filtrate was concentrated in vacuo to give a yellow oil, which was purified by chromatography on silica gel with elution by EtOAc/hexanes (2:8) to give the desired product (5.87 g, 66%) as a light yellow oil.

NMR (DMSO-d$_6$): δ 7.30 (m, 5H), 7.25 (d, J=8.7 Hz, 2H), 6.93 (d, J=8.7 Hz, 2H), 4.18 (t, J=7.0 Hz, 2H), 3.90 (s, 2H), 3.00 (t, J=7.0 Hz, 2H).

Step (2) Preparation of N'-Hydroxy-2-[4-(2-phenylethoxy)phenyl]ethanimidamide Hydroxylamine hydrochloride (3.40 g, 49.0 mmol), was added in one portion to a solution of sodium methoxide, freshly prepared from sodium (1.13 g, 49.0 mmol) in methanol (125 mL). The resulting mixture was stirred 1 hour at room temperature, during which a precipitate was formed. 4-(2-Phenylethoxy)phenylacetonitrile (5.8 g, 24.5 mmol) was added as a solution in a minimum volume of methanol and the resulting mixture stirred at room temperature 18 hours before being heated to reflux an additional 24 hours. The mixture was cooled to room temperature and concentrated in vacuo. The residue was partitioned between water (50 mL) and methylene chloride (100 mL), and the layers separated. The aqueous layer was extracted with methylene chloride (2×75 mL), and the combined organic layers were washed with water (2×50 mL), brine, dried over anhydrous sodium sulfate and concentrated in vacuo to give a yellow oil. The oil was dried in vacuo to give a yellow solid (5.21 g). The crude product was purified by chromatography on silica gel with elution by MeOH/CHCl$_3$ (2:98) to give the product (4.12 g, 62%).

NMR (DMSO-d$_6$): δ 8.82 (s, 1H), 7.25 (m, 5H), 7.15 (d, J=8.7 Hz, 2H), 6.83 (d, J=8.7 Hz, 2H), 5.35 (br s, 2H), 4.15 (t, J=7.0 Hz, 2H), 3.17 (s, 2H), 3.03 (t, J=7.0 Hz, 2H).

Step (3) Preparation of 4-[[4-(2-Phenylethoxy)phenyl]methyl]-3H-1,2,3,5-oxathiadiazole 2-Oxide A partial suspension of N'-hydroxy-2-[4-(2-phenylethoxy)phenyl]ethanimidamide (4.10 g, 15.2 mmol), in methylene chloride (160 mL) was treated with pyridine (6.00 g, 76.0 mmol) at room temperature. The resulting solution was cooled to 0° C. and treated with thionyl chloride (2.17 g, 18.2 mmol) which was added dropwise to give a dark yellow solution. The mixture was stirred 1 hour at 0° C., then diluted with water and the layers separated. The aqueous layer was extracted with methylene chloride (75 mL) and the combined organic layers were washed with water (3×150 mL), brine, dried over anhydrous sodium sulfate and concentrated in vacuo to give a dark oil (4.32 g). The crude product was purified by chromatography on silica gel with elution by EtOAc/hexanes (2:8) followed by recrystallization from EtOAc/hexanes to give pure product (0.66 g, 14%) as light yellow crystals, m.p. 96°–97° C.

NMR (DMSO-d$_6$): δ 11.39 (br s, 1H), 7.30 (m, 5H), 7.19 (d, J=8.7 Hz, 2H), 6.90 (d, J=8.7 Hz, 2H), 4.16 (t, J=7.0 Hz, 2H), 3.84 (s, 2H), 300 (t, J=7.0 Hz, 2H)

IR (KBr): 3360, 1620, 1520, 1390, 1250 cm$^{-1}$.

MS (EI): m/e 316 (M+), 237 (12), 105 (100).

Anal. Calcd. for $C_{16}H_{16}N_2O_3S$: C, 60.74; H, 5.10; N, 8.85%. Found: C, 60.60; H, 4.90; N, 8.78%.

EXAMPLE 3

4-[(4-Bromo-2-fluorophenyl)methyl]-3H-1,2,3,5-oxathiadiazole 2-Oxide

Step (1) Preparation of 4-Bromo-2-fluorophenylacetonitrile

KCN (2.91 g, 44.8 mmol) was added to a solution of 4-bromo-2-fluorobenzyl bromide (10.0 g, 37.3 mmol) in absolute ethanol (150 mL), and the resulting mixture heated to reflux for 18 hours. The mixture was cooled to room temperature and partitioned between water (100 mL) and ether (250 mL). The layers were separated and the aqueous layer reextracted with ether (150 mL). The combined organic layers were washed with water, brine, dried over anhydrous magnesium sulfate and concentrated in vacuo to give a light yellow oil. The oil was triturated with hexanes to give a white crystalline solid which was collected by filtration and dried in vacuo (3.93 g). The filtrate was concentrated and the residue purified by chromatography on silica gel with elution by EtOAc/hexanes (5:95) to give additional product (0.9 g). The solids were combined to give the desired product (total 4.83 g, 60%) of sufficient purity for use in the subsequent reaction.

NMR (DMSO-d$_6$): δ 7.63 (dd, J$_1$=9.2 Hz, J$_2$=1.3 Hz, 1H), 7.42 (m, 2H). 4.05 (s, 2H).

Step (2) Preparation of N'-Hydroxy-2-(4-bromo-2-fluorophenyl)ethanimidamide

Hydroxylamine hydrochloride (8.93 g, 128.5 mmol), was added in one portion to a solution of sodium methoxide, freshly prepared from sodium (2.96 g, 128.5 mmol) in methanol (200 mL). The resulting mixture was stirred 1 hour at room temperature, during which a precipitate was formed. 4-Bromo-2-fluorophenylacetonitrile (11.0 g, 51.4 mmol) was added and the resulting mixture heated to reflux for 20 hours. A white solid was removed by filtration of the hot mixture and discarded. The filtrate was concentrated to a volume of 100 mL to give a precipitate which was washed with water, followed by 5% EtOAc/hexanes. A second crop was obtained from the filtrate upon further concentration. The two crops were combined and dried in vacuo to give the product as a white crystalline solid (10.4 g, 82%) of sufficient purity for use in the subsequent reaction.

NMR (DMSO-$d_6$): $\delta$ 8.99 (s, 1H), 7.44 (dd, $J_1$=9.2 Hz, $J_2$=1.3 Hz, 1H), 7.32 (m, 2H), 5.47 (br s, 2H), 3.30 (s, 2H).

Step (3) Preparation of 4-[(4-Bromo-2-fluorophenyl)methyl]-3H-1,2,3,5-oxathiadiazole 2-Oxide A partial suspension of N'-hydroxy-2-(4-bromo-2-fluorophenyl)ethanimidamide (10.0 g, 40.5 mmol), in methylene chloride (300 mL) was treated with pyridine (16.0 g, 202.5 mmol) at room temperature. The resulting solution was cooled to 0° C. and treated with thionyl chloride (5.78 g, 48.6 mmol) which was added dropwise to give a golden brown solution. The mixture was stirred for 1.5 hours at 0° C., then diluted with water and the layers separated. The aqueous layer was extracted with methylene chloride (75 mL) and the combined organic layers were washed with water (2×150 mL), brine, dried over anhydrous sodium sulfate and concentrated in vacuo to give a brown oil. The oil was triturated with methylene chloride and ether to give a sticky brown solid. Recrystallization from methylene chloride/ether gave pure product (1.53 g, 13%) as a white crystalline solid, m.p. 124°–125° C.

NMR (DMSO-$d_6$): $\delta$ 7.57 (dd, $J_1$=9.6 Hz, $J_2$=1.9 Hz, 1H), 7.42 (dd, $J_1$=8.2 Hz, $J_2$=1.9 Hz, 1H), 7.34 (t, J=8.2 Hz, 1H), 3.97 (d, J=16.0 Hz, 1H), 3.92 (d, J=16.0 Hz, 1H).

IR (KBr): 3100, 1610, 1490, 1410, 1185 cm$^{-1}$.

MS (EI): m/e 292 (M+), 214 (46), 187 (100)

Anal. Calcd. for $C_8H_6BrFN_2O_2S$: C, 32.78; H, 2.06; N, 9.56%. Found: C, 32.97; H, 2.20; N, 9.51%.

EXAMPLE 4

4-[[(3-Trifluoromethyl)phenyl]methyl]-3H-1,2,3,5-oxathiadiazole 2-Oxide

Step (1) Preparation of N'-Hydroxy-2-(3-trifluoromethylphenyl)ethanimidamide m-(Trifluoromethyl)phenylacetonitrile (30.0 g, 0.16 mol) was added to a suspension of hydroxylamine hydrochloride (18.8 g, 0.27 mol), methanol (145 mL) and 25% sodium methoxide/methanol (62 mL, 0.27 mol) at room temperature. The reaction mixture was then heated to reflux for 2 hours, cooled and concentrated in vacuo. The residue was partitioned between methylene chloride and water. The organic layer was separated and dried over magnesium sulfate. The organic layer was concentrated in vacuo. The residue was purified by flash chromatography on silica gel with elution by hexane/ethyl acetate (8/2). The desired product (7.2 g, 21%) was obtained as a white solid, m.p. 91°–92° C.

NMR (acetone-$d_6$, 200 MHz): $\delta$ 3.5 (s, 2H), 5.2 (bs, 2H), 7.5 (m, 4H), 8.2 (bs, 1H).

MS (E/I): m/e 218.

Anal. Calcd. for $C_9H_9F_3N_2O$: C, 49.54; H, 4.16; N, 12.84%. Found: C, 49.39; H, 4.10; N, 12.78%.

Step (2) Preparation of 4-[[(3-Trifluoromethyl)phenyl]methyl]-3H-1,2,3,5-oxathiadiazole 2-Oxide A solution of thionyl chloride (9.6 mL) in methylene chloride (20 mL) was added to a mixture of N'-hydroxy-2-(3-trifluoromethylphenyl)ethanimidamide (7.2 g, 0.033 mol), pyridine (5.34 mL, 0.066 moL) and methylene chloride (100 mL) at 0° C. The resulting mixture was stirred 16 hours at room temperature and then poured into ice/water. The organic layer was separated, washed with saturated aqueous sodium chloride and dried over magnesium sulfate. Upon concentration in vacuo, a tan solid (6.0 g) was obtained. Recrystallization from ether/hexane afforded the desired product (2.1 g, 24%) as a light yellow solid, m.p. 132°–133° C.

NMR (DMSO-$d_6$, 400 MHz): $\delta$ 4.1 (s, 2H), 7.7 (m, 4H), 11.5 (bs, 1H)

MS (EI): m/e 264.

Anal. Calcd. for $C_9H_7F_3N_2O_2S$: C, 40.91; H, 2.67; N, 10.60%. Found: C, 40.68; H, 2.66; N, 10.52%.

The blood glucose lowering activity of the compounds of this invention was demonstrable in experiments using diabetic (db/db) mice. The db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia. Furthermore, the db/db mouse will eventually develop some of the long-term complications that have been associated with diabetes mellitus. [See Coleman *Diabetes* 31 (Suppl. 1), 1 (1982)]. In spite of these commonalities, the acute administration of sulfonylureas (even at extremely high dosages) will not reduce the hyperglycemia of the db/db mouse. [See Tutwiler et al, *Diabetes* 27, 856 (1978)]. The ability of a few other hypoglycemic agents to be effective in this species suggest that the other agents have mechanisms of action which are different from that of the sulfonylureas [ibid; Lee et al, *Diabetes* 31:12 (1982) Chang et al, *Diabetes* 32, 830 (1983); Hosokawa et al, *Diabetes* 34, 267 (1985)]. Such compounds, therefore, are more likely to be efficacious in the population of Type II diabetic patients that do not respond to sulfonylurea therapy. The experimental results are exemplified hereinbelow after the listing of the following general procedure pertaining to these experiments.

POSTPRANDIAL ASSAY PROCEDURE

On the morning of Day 1, 35 mice [male db/db (C57BL/KsJ), Jackson Laboratories, 2 to 7 months of age and body weight 35 to 60 g] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyser. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels:

| Group A: | Vehicle control | N = 6 |

| | | | |
|---|---|---|---|
| -continued | | | |
| Group B: | Positive control (ciglitazone) | N = 4 | |
| Group C: | 1st Test drug | N = 4 | |
| Group D: | 2nd Test drug | N = 4 | |
| Group E: | 3rd Test drug | N = 4 | |
| Group F: | 4th Test drug | N = 4 | |
| Group H: | 5th Test drug | N = 4 | |

On the afternoon of Days 1, 2 and 3 the vehicle, control or test drugs were administered (p.o.) to the ad libitum fed mice. The positive control, ciglitazone [(±)-5-[4-[(1-methylcyclohexy]methoxyl]benzyl]-thiazolidine-2,4-dione]see Fujita et al., *Diabetes* 32 804 (1983), was given by gavage at a dose of 100 mg/kg/day. The test compounds were given by gauage at a dose of 100 mg/kg/day unless otherwise noted in Table 1.

On the morning of Day 4, the mice were weighed and food removed, but water was available ad libitum. Three hours later, a blood sample was collected and then the mice were given the fourth administration of drug or vehicle. Blood samples were collected again from the unanesthetized mice at 2 and 4 hours after drug administration. The plasma was separated and levels of glucose in plasma determined by the Abbott VP Analyser.

For each mouse, the percent change of its plasma glucose level on Day 4 (mean of the 2 and 4 hour samples) from its respective level before drug administration (Day 1 baseline sample) was determined as follows:

$$\frac{\text{Mean of 2 and 4 hour Samples (Day 4)}}{\text{Baseline Sample (Day 1)}} \times 100$$

Analysis of variance followed by Dunnett's multiple comparison (one-sided) was used to estimate the degree of statistical significance of the difference between the vehicle control group and the individual drug-treated groups.

INSULIN TOLERANCE TEST ASSAY PROCEDURE

Alternatively, some compounds were evaluated for their ability to lower the plasma glucose of diabetic db/db mice during an insulin tolerance test (ITT).

On the morning of Day 1, 25 mice [male db/db (C57BL/KsJ), Jackson Laboratories, 2 to 7 months of age and body weight 35 to 60 g] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 20 mice were randomly assigned into 5 groups of equivalent mean plasma glucose levels:
Group A: Vehicle Control
Group B: Positive Control (ciglitazone)
Group C: 1st Test Drug
Group D: 2nd Test Drug
Group E: 3rd Test Drug On the afternoon of Days 1, 2, and 3, the vehicle, control or test drug were administered (p.o.) to the ad libitum fed mice. The mice were then fasted 18-24 hours and the fourth dose was administered on the morning of Day 4, immediately after the collection of the baseline blood sample. Additional blood samples were collected at 90 and 120 minutes after drug administration. Insulin was immediately administered (0.5 U/kg, s.c.) to every mouse after the 120 minutes sample. Serial blood samples were collected similarly at 45 and 120 minutes, after insulin administration (165 and 240 minutes, respectively, after the drug administration). The plasma was separated and levels of glucose in plasma determined by the Abbott VP Analyzer.

Analysis of variance followed by Dunnett's Multiple Comparison (one-sided) was used to estimate the degree of statistical significance of the difference between the plasma glucose level of the vehicle control and the individual drug-treated groups at each time. Statistical significance of the difference between the percent change of the vehicle control and the individual drug-treated groups at each time was determined by analysis of variance followed by Dunnett's Multiple Comparison (one-sided).

The tabulated results in Table 1 show that the oxathiadiazoles of this invention show the property that they lower blood glucose levels in the diabetic (db/db) mice using the postprandial assay procedure. The actual difference between the mean percent change of the vehicle and the drug-treated group is reported in Table 1.

TABLE 1

| $R^1$ | $R^2$ | Dose mg/kg/day | % Change from Vehicle in Postprandial Plasma Glucose | m.p. °C. |
|---|---|---|---|---|
| 3-CH$_3$ | 4-CH$_3$ | 20 | −17 | 127–130 |
| —H | | 20 | −5 | 96–97 |
| | 4-O—CH$_2$—CH$_2$—⟨phenyl⟩ | 100 | −56 | |
| 3-Cl | —H | 100 | −40 | 90–92 |

TABLE 1-continued

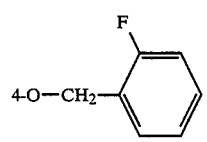

| R¹ | R² | Dose mg/kg/day | % Change from Vehicle in Postprandial Plasma Glucose | m.p. °C. |
|---|---|---|---|---|
| 3-CF₃ | —H | 20 | +5 | 132–133 |
| | | 100 | −34 | |
| 2-F | 4-Br | 100 | −28 | 124–125 |
| | | 20 | −17 | |
| —H | 4-Cl | — | — | 128–130 |
| —H | 4-O—CH₂— 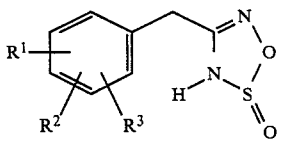 | 100 | −14 | 144–145.5 |
| —H | 4-O—CH₂—phenyl | 100 | −14 | 165–166 (dec.) |
| —H | 4-NO₂ | — | — | 141–144 (dec.) |
| 3-OCH₃ | 4-OCH₃ | — | — | 149–150 (dec.) |
| —H | 4-CF₃ | 20 | −7 | 140–141 |
| —H | 4-C(CH₃)₃ 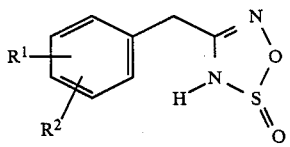 | 20 | −2 | 132–133 |
| —H | 4-phenyl | 20 | −1 | 163–164 (dec.) |
| Ciglitazone (reference standard) | | 100 | −33 | |

We claim:

1. The compounds of structural formula (I)

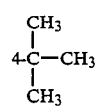

wherein R¹, R² and R³ are independently selected from the group consisting of hydrogen, lower alkyl or alkoxy containing 1 to 6 carbon atoms, halogen, trifluoromethyl, nitro, vinyl, ethynyl, alkylthio wherein alkyl contains 1 to 4 carbon atoms, nitrile, phenyl, phenyl- or halogen substituted phenylalkoxy wherein alkoxy contains 1 to 4 carbon atoms or the pharmaceutically acceptable salts thereof.

2. The compounds according to claim 1 of structural (II)

wherein R¹ is hydrogen, lower alkyl or alkoxy containing 1 to 2 carbon atoms, halogen or trifluoromethyl; R² is hydrogen, lower alkyl or alkoxy containing 1 to 6 carbon atoms, halogen, nitro, phenyl, phenyl or halogen substituted phenylalkoxy wherein alkoxy contains 1 to 2 carbon atoms or the pharmaceutically acceptable salts thereof.

3. The compound according to claim 2 4-[(3,4-dimethylphenyl)methyl]-3H-1,2,3,5-oxathiadiazole 2-oxide or the pharmaceutically acceptable salts thereof.

4. The compound according to claim 2 4-[[4-(2-phenylethoxy)phenyl]methyl]-3H-1,2,3,5-oxathiadiazole 2-oxide or the pharmaceutically acceptable salts thereof.

5. The compound according to claim 2 4-[(3-chlorophenyl)methyl]-3H-1,2,3,5-oxathiadiazole 2-oxide or the pharmaceutically acceptable salts thereof.

6. The compound according to claim 2 4-[[(3-trifluoromethyl)phenyl]methyl]-3H-1,2,3,5-oxathiadiazole 2-oxide or the pharmaceutically acceptable salts thereof.

7. The compound according to claim 2 4-[(4-chlorophenyl)methyl]-3H-1,2,3,5-oxathiadiazole 2-oxide or the pharmaceutically acceptable salts thereof.

8. The compound according to claim 2 4-[[4-[(2-fluorophenyl)methoxy]phenyl]methyl]-3H-1,2,3,5-oxathiadiazole 2-oxide or the pharmaceutically acceptable salts thereof.

9. The compound according to claim 2 4-[[4-(phenylmethoxy)phenyl]methyl]-3H-1,2,3,5-oxathiadiazole 2-oxide or the pharmaceutically acceptable salts thereof.

10. The compound according to claim 2 4-[(4-nitrophenyl)methyl]-3H-1,2,3,5-oxathiadiazole 2-oxide or the pharmaceutically acceptable salts thereof.

11. The compound according to claim 2 4-[(3,4-dimethoxyphenyl)methyl]-3H-1,2,3,5-oxathiadiazole 2-oxide or the pharmaceutically acceptable salts thereof.

12. The compound according to claim 2 4-[[4-(trifluoromethyl)phenyl]methyl]-3H-1,2,3,5-oxathiadiazole 2-oxide or the pharmaceutically acceptable salts thereof.

13. The compound according to claim 2 4-[[4-(1,1-dimethylethyl)phenyl]methyl]-3H-1,2,3,5-oxathiadiazole 2-oxide or the pharmaceutically acceptable salts thereof.

14. The compound according to claim 2 4-[(1,1'-biphenyl)-4-ylmethyl]-3H-1,2,3,5-oxathiadiazole 2-oxide or the pharmaceutically acceptable salts thereof.

15. The compound according to claim 2 4-[(4-bromo-2-fluorophenyl)methyl]-3H-1,2,3,5-oxathiadiazole 2-oxide or the pharmaceutically acceptable salts thereof.

16. A method of treating non-insulin dependent diabetes mellitus in humans by administering an effective amount of the compound of formula (I).

17. A pharmaceutical composition useful for treating non-insulin dependent diabetes mellitus in humans comprising an effective amount of a compound of formula (I) and a pharmaceutically acceptable carrier.

* * * * *